(12) United States Patent
Förtsch et al.

(10) Patent No.: US 8,909,315 B2
(45) Date of Patent: Dec. 9, 2014

(54) GASTROSCOPE

(75) Inventors: Stefan Förtsch, Kunreuth (DE); Rainer Kuth, Höchstadt (DE); Karl-Heinz Maier, Altdorf b. Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 595 days.

(21) Appl. No.: 13/148,506

(22) PCT Filed: Feb. 15, 2010

(86) PCT No.: PCT/EP2010/051855
§ 371 (c)(1),
(2), (4) Date: Aug. 9, 2011

(87) PCT Pub. No.: WO2010/094651
PCT Pub. Date: Aug. 26, 2010

(65) Prior Publication Data
US 2011/0313265 A1    Dec. 22, 2011

(30) Foreign Application Priority Data

| Feb. 17, 2009 | (DE) | 10 2009 009 290 |
| May 28, 2009 | (DE) | 10 2009 023 037 |
| Feb. 5, 2010 | (DE) | 10 2010 006 969 |

(51) Int. Cl.
| A61B 5/1468 | (2006.01) |
| A61B 5/1473 | (2006.01) |
| A61B 5/05 | (2006.01) |
| A61B 5/00 | (2006.01) |
| A61B 5/053 | (2006.01) |
| A61B 1/273 | (2006.01) |
| A61B 1/00 | (2006.01) |
| A61B 5/145 | (2006.01) |
| A61B 18/12 | (2006.01) |

(52) U.S. Cl.
CPC .............. *A61B 5/053* (2013.01); *A61B 5/6852* (2013.01); *A61B 5/0538* (2013.01); *A61B 2018/126* (2013.01); *A61B 5/4238* (2013.01); *A61B 1/2736* (2013.01); *A61B 1/0008* (2013.01); *A61B 5/14546* (2013.01)
USPC .......................................... 600/350; 600/380

(58) Field of Classification Search
USPC ......... 600/309, 345, 348, 349, 350, 361, 380, 600/547, 302
See application file for complete search history.

(56) References Cited

U.S. PATENT DOCUMENTS 3,340,866 A * 9/1967 Noller ........................... 600/302
5,477,854 A * 12/1995 Essen-Moller ............... 600/350

(Continued)

FOREIGN PATENT DOCUMENTS

| CN | 2458626 | 11/2001 |
| EP | 1 284 120 A1 | 2/2003 |

(Continued)

OTHER PUBLICATIONS

Stefan Foertsch et al., "Development of a new electrochemical device for rapid helicobacter pylori detection," Vortrag anlässlich der Digestive Disease Week in New Orleans, 1.-5. May 2010.

(Continued)

*Primary Examiner* — Navin Natnithithadha
(74) *Attorney, Agent, or Firm* — Schiff Hardin LLP

(57) ABSTRACT

A gastroscope has an insertion tube with a distal end, at which a sensor is located. The sensor has a first electrode produced of an acid-resistant noble metal, and a second electrode produced of silver. An electrical voltage is applied between the first and second electrodes, and a change in an electrical variable is measured between the first and second electrodes, when ammonia is present. The gastroscope allows screening of gastric acid and the tissue of the stomach lining for *Helicobacter pylori* in a manner that is gentle for the patient.

19 Claims, 1 Drawing Sheet

(56) References Cited

U.S. PATENT DOCUMENTS

| | | | |
|---|---|---|---|
| 5,507,289 | A | 4/1996 | Essen-Moller |
| 5,556,760 | A * | 9/1996 | Nakamura et al. ............. 435/12 |
| 6,405,732 | B1 | 6/2002 | Edwards et al. |
| 6,419,809 | B1 * | 7/2002 | Suzuki et al. ................. 204/435 |
| 6,479,278 | B2 | 11/2002 | Marshall |
| 2001/0012623 | A1 | 8/2001 | Marshall |
| 2003/0060702 | A1 | 3/2003 | Kuth et al. |
| 2004/0176664 | A1 | 9/2004 | Iddan |
| 2005/0043583 | A1 * | 2/2005 | Killmann et al. ............. 600/109 |
| 2005/0069932 | A1 * | 3/2005 | Arinaga et al. ................. 435/6 |
| 2005/0096502 | A1 | 5/2005 | Khalili |
| 2005/0148847 | A1 * | 7/2005 | Uchiyama et al. ........... 600/407 |
| 2005/0192478 | A1 * | 9/2005 | Williams et al. ............. 600/160 |
| 2007/0021654 | A1 * | 1/2007 | Preidel et al. ................. 600/160 |
| 2007/0138027 | A1 | 6/2007 | Dinsmoor et al. |
| 2008/0200788 | A1 | 8/2008 | Brister et al. |
| 2008/0255409 | A1 * | 10/2008 | Graumann et al. ........... 600/101 |
| 2011/0092787 | A1 * | 4/2011 | Bulitta et al. ................. 600/364 |

FOREIGN PATENT DOCUMENTS

| | | |
|---|---|---|
| JP | 07323034 A | 12/1995 |
| JP | 09206095 A | 8/1997 |
| WO | WO 2007/020410 A1 | 2/2007 |

OTHER PUBLICATIONS

Helmut Neumann et al., "Immediate detection of Helicobacter infection with a novel electrochemical system: Feasibility and comparison of diagnostic yield with immunohistochemistry, 13C urea breath test and Helicobacter urease test," Vortrag analässlich der Digestive Disease Week in New Orleans, 1.-5, May 2010.

"Helicobacter-Antigen im Stuhl," Laborlexikon.de, Facharztwissen für alle, e-Journal für Labormedizin, http://www.laborlexikon.de/Lexikon/Infoframe/h/Helicobacter-Atemtest.htm.

"Helicobacter-Atemtest," Laborlexikon.de, Facharztwissen für alle, e-Journal für Labormedizin, http://www.laborlexikon.de/Lexikon/Infoframe/h/Helicobacter-Atemtest.htm.

Wataru Satoh et al., Highly Sophisticated Electrochemical Analysis System with an Integrated Microfluidic System Based on Electrowetting, IEEE Sensors 2006, EXCO, Daegu, Korea, Oct. 22-25, 2006, pp. 1004-1007.

Vortrag von Jürgen Lorenzen, Olympus, "Erfahrungsaustausch zur Schadensprävention in der Endoskopie," 2. FKT-Fortbildungsveranstaltung 2008, Landesgruppe Hamburg am Sep. 25, 2008.

Marko Petack, Olympus Deutschland GmbH, Präsentation mit dem Titel "Gerätetechnik Flexible Endoskope," 2008.

Xiaobo Ji et al., "The electrochemical oxidation of ammonia at boron-doped diamond electrodes exhibits analytically useful signals in aqueous solutions," Analyst, vol. 130 (2005), S. 1345-1347.

"Menschen tragen seit 60.000 Jahren blinden Passagier im Bauch," Spiegel Online, 2007, http://www.spiegel.de/wissenschaft/mensch/0,1518,464986,00.html.

Satoh et al."Highly Sophisticated Electrochemical Analysis System with an Integrated Microfluidic System Based on Electrowetting," IEEE Sensors, pp. 1004-1007 (2006).

* cited by examiner

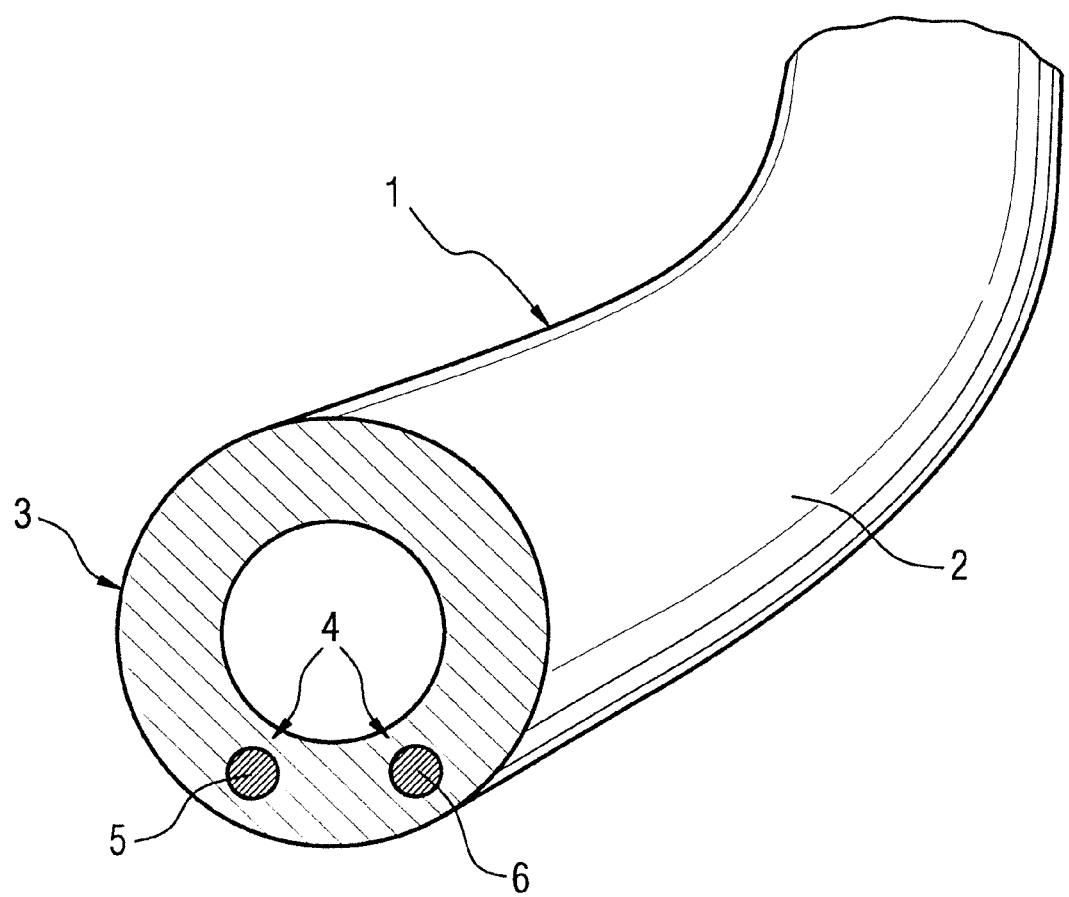

GASTROSCOPE

BACKGROUND OF THE INVENTION

1. Field of the Invention

The invention relates to a gastroscope.

Such a gastroscope, which is a flexible endoscope, serves for examining the upper gastrointestinal tract.

2. Description of the Prior Art

A common cause for discomforts in the upper gastrointestinal tract is a bacterial affliction of the organs therein. For example, an affliction with *Helicobacter pylori* is responsible for a vast range of gastric disorders that are associated with an increased secretion of gastric acid. For example, these include type B gastritis, approximately 75% of gastric ulcers and almost all duodenal ulcers. Hence, examining the hollow organs of the gastrointestinal tract for bacteria populations, more particularly *Helicobacter pylori* populations, is an important component for diagnosing gastric disorders.

For example, *Helicobacter pylori* is detected using a breath test, in which a patient is administered C-13 masked urea. The C-13 masked $CO_2$, which is created when urea $(CO(NH_2)_2)$ is split into ammonia $(NH_3)$ and carbon dioxide $(CO_2)$, is detected in the exhaled air. Other methods for detecting *Helicobacter pylori* are directed at typical blood values such as pepsinogen or gastrin. However, such methods are complex and only have limited reliability. A further test for *Helicobacter pylori* is the detection of the *Helicobacter pylori* antigen in fecal matter.

A further option for examining the stomach for a *Helicobacter pylori* population is provided by so-called gastroscopy. During such an examination, a gastroenterologist takes a tissue sample (biopsy specimen) from the mucosa of the stomach by means of a biopsy in order to examine, either immediately or at a later stage, whether there is an infection with *Helicobacter pylori*. A known examination method for the tissue sample is, for example, the *Helicobacter* urease test (HU test, abbreviated HUT). The biopsy specimen is placed into a test medium (measurement solution), which consists of a nutrient solution for this bacteria, urea, and an indicator (litmus). If *Helicobacter pylori* bacteria is contained in the sample, the bacteria splits the urea $(CO(NH_2)_2)$ using urease into ammonia $(NH_3)$ and carbon dioxide $(CO_2)$. The ammonia then colors the indicator red. The test result is ready after a few minutes. The onset of color change from yellow to red cannot unambiguously be identified in inexpedient conditions.

An alternative to gastroscopy carried out using a flexible endoscope consists of using a so-called endoscopic capsule. Such an endoscopic capsule, which is also referred to as a capsule endoscope or endocapsule, is embodied as a passive endocapsule or a navigable endocapsule. A passive endoscopic capsule moves through the intestines of the patient as a result of peristalsis.

For example, a navigable endocapsule is known from patent DE 101 42 253 C1 and the corresponding patent application US 2003/0060702 A1, and therein it is referred to as an "Endoroboter" or "endo-robot". The endo-robot known from these publications can be navigated in a hollow organ (e.g. gastrointestinal tract) of a patient by means of a magnetic field, which is generated by an external (i.e. arranged outside of the patient) magnetic system (coil system). An integrated system for controlling the position, that includes a positional measurement of the endo-robot and automatic regulation of the magnetic field or the coil currents, can be used to detect changes automatically in the position of the endo-robot in the hollow organ of the patient and to compensate for these. Furthermore, the endo-robot can be navigated to desired regions of the hollow organ in a targeted fashion. It is for this reason that this type of capsule endoscopy is also referred to as magnetically guided capsule endoscopy (MGCE).

SUMMARY OF THE INVENTION

An object of the present invention is to provide a gastroscope that can be used to test the gastric acid and the tissue of the mucosa of the stomach for *Helicobacter pylori* within a very short period of time.

The gastroscope according to the invention has an insertion tube, at the distal end of which a sensor is arranged, wherein the sensor comprises a first electrode made of a noble metal, which cannot be attacked by acid (e.g. hydrochloric acid, phosphoric acid, sulfuric acid, gastric acid), and a second electrode made of silver. An electric voltage can be applied between the first electrode and the second electrode, and a change in an electric variable can be measured if ammonia is present between the first electrode and the second electrode.

In the gastroscope according to the invention, ammonia $(NH_3)$ can in a simple fashion be detected directly in the gastrointestinal tract of a patient during the examination, without taking a tissue sample. The gastroscope according to the invention therefore allows an examination of the gastric acid and the tissue of the mucosa of the stomach for *Helicobacter pylori* that does not put much strain onto the patient.

In a preferred gastroscope according to the invention, the electric voltage between the first electrode and the second electrode equals zero. Thus no current flows between the first electrode and the second electrode. Advantageously, the potential is thereby measured (i.e. without a current) between the first electrode and the second electrode. Thus there is hardly any ionic migration in the gastric acid.

In a further advantageous embodiment, the electric voltage between the first electrode and the second electrode is an AC voltage with a variably predeterminable frequency spectrum. If gastric acid is exposed to direct current or a directed potential the ions migrate to the associated electrodes, i.e. the cations (e.g. ammonium $NH_4^+$) migrate to the cathode and the anions (e.g. chloride $Cl^-$) migrate to the anode. By applying a suitable AC voltage, the gastroscope according to the invention reliably prevents complete charging of the first electrode (reference electrode) and complete charging of the second electrode (measurement electrode) because the migration speed of the ions in the gastric acid is almost zero if the frequency is sufficiently high.

When an AC voltage is applied, there is a cyclical change at the second electrode (measurement electrode), which, according to the invention, consists of silver (Ag), between destruction and buildup of the silver chloride (AgCl) layer. Both the destruction of the silver chloride layer and the buildup thereof can be measured by e.g. an impedance measurement and can be compared cyclically. The potential differences and phase differences that can be measured in the process are characteristic for the presence of urease activity, as a result of which presence of *Helicobacter pylori* can be deduced with a very high certainty.

In a further embodiment, the frequency spectrum of the AC voltage is modulated. As a result, a higher AC voltage stability is obtained, which increases the measurement accuracy and reduces the measurement duration.

In another embodiment, the electric voltage between the first electrode and the second electrode is a DC voltage, which can be applied for a predeterminable period of time. The predeterminable period of time during which an electric voltage can be applied by the user between the first electrode and the second electrode may lie between zero seconds and continuously, wherein the electric voltage selected by the user may be zero volts or higher. In the case of a period of time of zero seconds or a voltage of zero volts, this is a passive measurement. In the case of values deviating from these, this is an active measurement.

As per advantageous embodiments of the gastroscope according to the invention, e.g. potentials, electric currents or electric resistances or the changes therein or variables (e.g. electric conductivity) derived from the electric variables or changes therein can be measured as electric variables.

The second electrode (measurement electrode), which consists of silver (Ag) in the case of the gastroscope according to the invention, must be etched by hydrochloric acid (HCl). This may (but this is not necessary) already occur for the first time before the gastroscope or the second electrode is supplied. However, it is also possible for the users themselves to undertake the initial HCl etching or apply an appropriate silver chloride layer by means of a suitable electrolytic method. After HCl etching or after electrolytic deposition, the second electrode has a silver chloride (AgCl) coating on its surface and is therefore activated for the measurement to detect *Helicobacter pylori*.

Using the gastroscope according to claim 1, ammonia ($NH_3$) can in a simple fashion be detected directly in the gastrointestinal tract of a patient during the examination, without taking a tissue sample.

The gastroscope according to the invention allows simple open or closed loop control of the sensor or its first electrode (reference electrode) and/or its second electrode (measurement electrode) e.g. by means of a baseline correction. Furthermore, a reproducible regeneration of the sensor, more particularly the second electrode, is possible after each examination.

If the measures outlined above are taken, the second electrode is not completely charged, and so a regeneration of the second electrode only becomes necessary after a multiplicity of examinations.

Moreover, the sensitivity of the sensor and/or its first and/or second electrode can be set in a simple fashion in the gastroscope according to the invention. The sensitivity can be set before and during the examination in respect of *Helicobacter pylori*.

Platinum (Pt) and gold (Au) can be used as noble metals that are not attacked by acid and therefore are suitable for the first electrode (reference electrode).

After inserting the gastroscope according to the invention, the sensor detects ammonia ($NH_3$) present in the gastric acid and in the tissue of the mucosa of the stomach on the stomach inner wall. This is used to detect affliction of the tissue (mucosa of the stomach) with *Helicobacter pylori* in a patient-friendly fashion by detecting ammonia ($NH_3$). This takes place without a biopsy and therefore puts much less strain on the patient.

The detection of ammonia is a very strong indication for the presence of *Helicobacter pylori* because ammonia is generated by the *Helicobacter pylori* bacteria by splitting urea using urease in order to protect itself from the acidic environment of the gastrointestinal tract, more particularly the high acid concentration in the stomach.

As noted above, second electrode (measurement electrode), which consists of silver (Ag) in the gastroscope according to the invention, must be etched by hydrochloric acid (HCl). After the HCl etching, the second electrode has a silver chloride (AgCl) coating on its surface and is therefore activated for the measurement to detect *Helicobacter pylori*. The activation of the second electrode is based on the following chemical reaction:

$$Ag + HCl \rightarrow AgCl + H^+ + e^-$$

Since ammonia ($NH_3$) under normal circumstances does not occur, or only occurs in very low concentrations in a hollow organ of the gastrointestinal tract, such as the stomach, as a result of the following neutralization reaction (forming an ammonium cation by protonation of ammonia)

$$NH_3 + H^+ \square NH_4^+$$

the detection thereof is a very strong indication for the presence of *Helicobacter pylori*. The proton ($H^+$, hydrogen nucleus) is a component of the gastric acid.

The corresponding chemical reaction for detecting *Helicobacter pylori* is:

$$AgCl + 2NH_3 \rightarrow [Ag(NH_3)_2]^+ + Cl^-$$

The AgCl salt (silver chloride) is split into the silver-diammine complex $[Ag(NH_3)_2]^+$ and chloride $Cl^-$ by ammonia. $[Ag(NH_3)_2]^+$ as a cation is very soluble in water and absorbed by the gastric acid. As per advantageous embodiments of the gastroscope according to the invention, there is between the first electrode (reference electrode) and second electrode (measurement electrode) either an electric voltage of zero or an electric AC voltage with a variably predeterminable frequency spectrum Alternatively, a DC voltage can be applied between the first electrode and the second electrode for a predeterminable period of time. In all cases, there is barely any ion migration in the gastric acid (migration speed of the cations and anions is approximately zero).

The electric variable (potential, electric current, electric resistance) measured between the first electrode (reference electrode) and second electrode (measurement electrode) is recorded, displayed, and—if desired—transmitted to evaluation electronics. As a result of an (automated) comparison between the measured value and predetermined values, a possible affliction of the mucosa of the stomach with *Helicobacter pylori* can be reliably indicated.

By rinsing the second electrode with hydrochloric acid, the silver chloride layer on the second electrode is regenerated. The damage to the silver chloride layer of the second electrode caused by ammonia is thereby removed again. The gastroscope according to the invention can thus once again be used for detecting *Helicobacter pylori* after a possible necessary recalibration of the sensor. By way of example, the sensor can be calibrated by a dose of synthetic ammonia. After the gastroscopy is completed, the gastroscope is removed and subsequently disinfected. In order to remove still present remains of AgCl it is expedient to clean the sensor using an ammoniacal rinsing solution (e.g. an ammoniacal disinfectant). If the gastroscope has a sensor with a suitable design, the gastroscope can be completely sterilized by a suitable sterilization method and can be used for another examination.

The gastroscope according to the invention allows an examination, which only puts little strain on the patient, of the mucosa of the stomach in respect of *Helicobacter pylori*, wherein tissue samples are only taken if the presence of *Helicobacter pylori* is suspected. The gastroscope can take tissue samples if it has a biopsy apparatus.

BRIEF DESCRIPTION OF THE DRAWINGS

The single FIGURE substantially illustrates a gastroscope in accordance with the invention.

DESCRIPTION OF THE PREFERRED EMBODIMENTS

The invention and further advantageous embodiments are explained in more detail below in the drawing on the basis of a schematically illustrated exemplary embodiment; however, the invention is not restricted to the explained exemplary embodiment.

The only FIGURE shows a gastroscope 1, which is a flexible endoscope and serves for examining the upper gastrointestinal tract.

The gastroscope 1 has a flexible insertion tube 2, on the one end of which, more particularly on the distal end 3 of which, a sensor 4 is arranged. The sensor 4 comprises a first electrode 5 (reference electrode) made of a noble metal, which cannot be attacked by hydrochloric acid, and a second electrode 6 (measurement electrode) made of silver (Ag).

In the illustrated exemplary embodiment both electrodes 5 and 6 have a constant distance from one another.

Platinum (Pt) and gold (Au) can be used as noble metals that are not attacked by hydrochloric acid and therefore are suitable for the first electrode 5.

An electric voltage can be applied between the first electrode 5 and the second electrode 6, as a result of which a change in an electric variable, e.g. potential, electric current, or electric resistance, can be measured if ammonia is present between the first electrode 5 and the second electrode 6.

In the illustrated exemplary embodiment, the sensor 4 and/or the first electrode 5 and/or the second electrode 6 are arranged on the end face at the distal end 3 of the insertion tube 2 of the gastroscope 1. Other arrangements of the sensor 4 and/or the first electrode 5 and/or the second electrode 6 are also possible within the scope of the invention. Thus, e.g. at least one of the two electrodes 5 and 6 can be arranged in the side wall of the insertion tube 2 such that there is no need to increase the diameter of the insertion tube 2 of the gastroscope 1.

Further elements such as e.g. optical waveguides (fiber bundles coupled to a light source) and image waveguides (fiber bundles coupled to a camera) and deflection cables (running in the flexible outer shell of the gastroscope) may be arranged in the gastroscope 1 illustrated in the drawing. The further elements, the arrangement of which is known per se, are not illustrated in the drawing for reasons of clarity.

Although modifications and changes may be suggested by those skilled in the art, it is the intention of the inventors to embody within the patent warranted heron all changes and modifications as reasonably and properly come within the scope of their contribution to the art.

We claim as our invention therefor:

1. A gastroscope comprising:
   an insertion tube having a size and shape allowing insertion of said insertion tube into the gastrointestinal tract of a subject, said insertion tube having a distal end;
   a sensor at said distal end of said insertion tube that is exposed to an interior of the gastrointestinal tract, said sensor comprising a first electrode made of a noble metal, which cannot be attacked by acid and a second electrode made of silver with a silver chloride layer that is exposed to said interior;
   a voltage source connected between said first electrode and said second electrode that produces an electric voltage between said first electrode and said second electrode with said first electrode operated as a reference electrode and said second electrode operated as a measurement electrode; and
   a detector that detects a change in an electrical variable between said first electrode and said second electrode when ammonia is present in said interior between said first electrode and said second electrode, by said silver chloride layer participating in a chemical reaction with said ammonia.

2. A gastroscope as claimed in claim 1 wherein said voltage source produces an electric voltage between said first electrode and said second electrode of zero.

3. A gastroscope as claimed in claim 1 wherein said voltage source produces said electric voltage source as an AC voltage with a variable frequency spectrum.

4. A gastroscope as claimed in claim 1 wherein said voltage source produces said electric voltage as a DC voltage for a predetermined period of time.

5. A gastroscope as claimed in claim 1 wherein said detector measures electrical potential as said electrical variable.

6. A gastroscope as claimed in claim 1 wherein said detector measures electrical current as said electrical variable.

7. A gastroscope as claimed in claim 1 wherein said detector measures electrical resistance as said electrical variable.

8. A gastroscope as claimed in claim 1 wherein said first electrode is made of a noble metal selected from the group consisting of platinum and gold.

9. A gastroscope as claimed in claim 1 wherein at least one of said first electrode and said second electrode is configured to be replaceable.

10. A gastroscope as claimed in claim 1 wherein said second electrode is regenerable.

11. A gastroscope as claimed in claim 1 wherein said insertion tube comprises a work channel and wherein said sensor is located in the insertion tube next to said work channel.

12. A gastroscope as claimed in claim 1 wherein said sensor is located at an exterior surface of the insertion tube.

13. A gastroscope as claimed in claim 1 wherein said voltage source generates said electrical voltage as an AC sinusoidal voltage.

14. A gastroscope as claimed in claim 1 wherein said voltage source generates said electrical voltage as an AC triangular voltage.

15. A gastroscope as claimed in claim 1 wherein said voltage source generates said electrical voltage as an AC sawtooth voltage.

16. A gastroscope as claimed in claim 1 wherein said voltage source generates said electrical voltage as an AC voltage representing a noise spectrum.

17. A gastroscope as claimed in claim 1 wherein said voltage source generates said electrical voltage as an AC voltage having a variable frequency spectrum comprised of at least two pulses with respectively different shapes.

18. A gastroscope as claimed in claim 1 wherein said voltage source generates said electrical voltage as an AC voltage with a variable frequency spectrum comprised of components having respectively different bandwidths.

19. A gastroscope as claimed in claim 1 wherein said voltage source generates said electrical voltage as a modulated AC voltage having a variable frequency spectrum.

* * * * *